(12) United States Patent
Houze et al.

(10) Patent No.: US 11,304,981 B2
(45) Date of Patent: Apr. 19, 2022

(54) PLATELET LYSATE GEL

(71) Applicant: Cell Therapy Limited, Swansea (GB)

(72) Inventors: Thomas Averell Houze, Boras (SE);
Martin John Evans, Cardiff (GB);
Ajan Trevor Reginald, Cardiff (GB);
Ina Laura Pieper, Swansea (GB)

(73) Assignee: Cell Therapy Limited, Swansea (GB)

( * ) Notice: Subject to any disclaimer, the term of this patent is extended or adjusted under 35 U.S.C. 154(b) by 360 days.

(21) Appl. No.: 16/165,627

(22) Filed: Oct. 19, 2018

(65) Prior Publication Data

US 2019/0160104 A1 May 30, 2019

Related U.S. Application Data

(62) Division of application No. 15/667,538, filed on Aug. 2, 2017, now Pat. No. 10,117,898, which is a division of application No. 14/360,286, filed as application No. PCT/GB2012/052911 on Nov. 23, 2012, now abandoned.

(30) Foreign Application Priority Data

| Nov. 23, 2011 | (GB) | 1120224 |
| Nov. 23, 2011 | (GB) | 1120230 |
| Nov. 23, 2011 | (GB) | 1120231 |
| Nov. 23, 2011 | (GB) | 1120235 |

(51) Int. Cl.

| A61K 35/19 | (2015.01) |
| A61K 8/27 | (2006.01) |
| A61K 8/43 | (2006.01) |
| A61K 8/44 | (2006.01) |
| A61K 8/49 | (2006.01) |
| A61K 8/64 | (2006.01) |
| A61K 8/73 | (2006.01) |
| A61K 8/04 | (2006.01) |
| A61K 8/19 | (2006.01) |
| A61K 8/98 | (2006.01) |
| A61K 9/00 | (2006.01) |
| A61L 26/00 | (2006.01) |
| A61Q 19/08 | (2006.01) |
| C12N 5/078 | (2010.01) |
| A61K 8/72 | (2006.01) |
| A61K 8/96 | (2006.01) |
| A61K 35/12 | (2015.01) |
| A61K 35/16 | (2015.01) |
| A61K 35/33 | (2015.01) |

(52) U.S. Cl.
CPC .......... *A61K 35/19* (2013.01); *A61K 8/042* (2013.01); *A61K 8/19* (2013.01); *A61K 8/27* (2013.01); *A61K 8/43* (2013.01); *A61K 8/44* (2013.01); *A61K 8/447* (2013.01); *A61K 8/4913* (2013.01); *A61K 8/4946* (2013.01); *A61K 8/64* (2013.01); *A61K 8/72* (2013.01); *A61K 8/731* (2013.01); *A61K 8/96* (2013.01); *A61K 8/983* (2013.01); *A61K 9/0014* (2013.01); *A61K 9/0031* (2013.01); *A61K 9/0034* (2013.01); *A61K 35/12* (2013.01); *A61K 35/16* (2013.01); *A61K 35/33* (2013.01); *A61L 26/008* (2013.01); *A61L 26/0019* (2013.01); *A61L 26/0023* (2013.01); *A61L 26/0061* (2013.01); *A61Q 19/08* (2013.01); *C12N 5/0644* (2013.01); *A61K 2800/524* (2013.01); *A61L 2300/30* (2013.01)

(58) Field of Classification Search
None
See application file for complete search history.

(56) References Cited

U.S. PATENT DOCUMENTS

| 5,180,723 A * | 1/1993 | Whittaker | A61P 43/00 514/234.2 |
| 5,198,357 A | 3/1993 | Holmovist et al. | |
| 5,457,093 A | 10/1995 | Cini et al. | |
| 8,603,821 B2 | 12/2013 | Suzuki et al. | |
| 2010/0120150 A1 | 5/2010 | Suzuki et al. | |
| 2010/0278783 A1 | 11/2010 | Rouy et al. | |

FOREIGN PATENT DOCUMENTS

| JP | 2008246200 A | 10/2008 |
| JP | 2011219428 A | 11/2011 |
| RU | 2138162 C1 | 9/1999 |
| WO | 2010/033605 A2 | 3/2010 |
| WO | 2010064267 A1 | 6/2010 |
| WO | 2013005053 A2 | 1/2013 |

OTHER PUBLICATIONS

"Physical Properties of Natural Gas" website (https://sciencing.com/physical-properties-nitrogen-gas-2719.html)—accessed Oct. 2020.*
Ranzato E et al. "Platelet lysate stimulates wound repair of HaCaT keratinocytes", British Journal of Dermatology Oxford: Wiley-Blackwell. UK, vol. 159, No. 3, Sep. 1, 2008, pp. 537-545.
Clayton and Elasy, "A Review of the Pathophysiology, Classification, and Treatment of Foot Ulcers in Diabetic Patients", Clinical Diabetes, 2009, vol. 27, No. 2, pp. 52-58.
Jeffcoate et al., "Randomised controlled trial of the use of three dressing preparations in the management of chronic ulceration of the foot in diabetes", Health Technology Assessment, 2009, vol. 13, No. 54.
Singh et al., "Preventing Foot Ulcers in Patients With Diabetes" JAMA, Jan. 12, 2005, vol. 293, No. 2, pp. 217-228.

(Continued)

*Primary Examiner* — Susan Hoffman
(74) *Attorney, Agent, or Firm* — Norton Rose Fulbright US LLP

(57) ABSTRACT

The invention concerns a pharmaceutical composition comprising a platelet lysate and its use to treat a wound, an anal fissure, vaginal atrophy or a wrinkle.

1 Claim, 7 Drawing Sheets

(56) References Cited

OTHER PUBLICATIONS

Reiber et al., "Causal Pathways for Incident Lower-Extremity Ulcers in Patients With Diabetes From Two Settings", Diabetes Care, 1999, 22: 157-162.

Dougherty, "An Evidence-Based Model Comparing the Cost-effectiveness of Platelet-Rich Plasma Gel to Alternative Therapies for Patients with Nonhealing Diabetic Foot Ulcers", Adv Skin Wound Care, 2008, 21(12): 568-75.

Mazzucco et al., "Not every PRP-gel is born equal Evaluation of growth factor availability for tissues through four PRP-gel preparations: Fibrinet®, RegenPRP-Kit®, Plateltex® and one manual procedure", Vox Sang, 2009, 97(2): 110-118.

Greppi et al., "Treatment of recalcitrant ulcers with allogeneic platelet gel from pooled platelets in aged hypomobile patients", Biologicals, 2011, 39(2): 73-80.

Aghabeigi et al., "Identification and Characterization of Anti-Platelet Antibodies in Idiopathic Thrombocytopenic Purpura Patients", Iranian J Publ Health, vol. 41, No. 2., 2012, pp. 53-62.

Plöderl et al., "Development and validation of a production process of platelet lysate for autologous use", Platelets, May 2011; 22(3): pp. 204-209, Informa UK Ltd.

Chinese Office Action dated Jul. 13, 2016 during prosecution of related CN. Appl. No. 201280067727.0 (with English translation).

Hong-Tao et al., "Freeze-thaw by Liquid nitrogen promotes platelet-dervied growth factor-AA and transforming growth factor-β1 release", J. Clinical Rehabilitative Tissue Engineering Research, 2010, vol. 14, No. 36, pp. 6764-6767.

Japanese Office Action dated Sep. 20, 2016 during prosecution of JP Appl. No. 2014-542934.

Gruber et al., "Platelets are mitogenic for periosteum-derived cells", Journal of Orthopaedic Research, Feb. 2003, No. 21, pp. 941-948.

Eurasian Search Report dated Jun. 21, 2018 during prosecution of related Eurasian Patent Application No. 201792475/26.

Mirabet et al. "Human platelet lysate enhances the proliferative activity of cultured human fibroblast-like cells from different tissues", Cell Tissue Banking, 2008, 9:1-10.

* cited by examiner

CTL WRINKLE REDUCTION PLATFORM

| | | Treatment Time (min) | Allergy | Cost per treatment | Treatments[2] | Total cost |
|---|---|---|---|---|---|---|
| RADIESSE® RESTYLANE® JUVEDERM® SCULPTRA® REGRANEX® | 1° generation | Molecules: Dermal Fillers and Individual Growth Factors | 15 | Possible | ~$1,000 | 6 | ~$6,000 |
| SELPHYL® LAVIV® MYCELLS® | 2° generation | Autologous Cell therapy: Platelet-Rich Plasma or Fibroblasts | PRP: 50 laViv: 15[1] | No | ~$2,000 | 3 | ~$6,000 |
| CELL THERAPY LTD™ | 3° generation | Cell therapy Isolate: Standardized product with platelet and Growth factors | 15 | No | ~$1,000 | 1 | ~$1,000 |

FIG. 2

PLATELET THERAPY QUALITY CONTROLS

| | Source | Production | Functionality Test |
|---|---|---|---|
| PLATELTEX® AUTOLOGEL® CYTOMEDIX® 2° generation | • Autologous source translated to variable platelet count and quality dependent on patient health status | • Multi-step, in-office manipulation and lack of quantitation introduced variability, errors and potential contamination | • No functional of product before patient application |
| CELL THERAPY LTD™ 3° generation | • Quality controlled source of *in vitro* platelets ensures high quality contamination free platelets | • Precise quantification of product component ensures standardized product | • Automated ECIS (Electric Cell-substrate Impedance Sensing) wound healing assay to confirm efficacy |

FIG. 5

PLATELET LYSATE GEL

FIELD OF THE INVENTION

The invention concerns a pharmaceutical composition comprising a platelet lysate and its use to treat a wound, an anal fissure, vaginal atrophy or a wrinkle.

BACKGROUND OF THE INVENTION

Approximately 15% diabetics will have an ulcer in their lifetime. Annual, population-based incidence of 1% to 3.6% among people with type 1 or type 2 diabetes. By 2030, approximately 13 million people will suffer a diabetic foot ulcer each year. Foot ulcers precede more than 84% of non-traumatic lower limb amputations. In addition, the 3-year mortality after a first amputation has been estimated as high as 20-50%. The average cost of healing a single ulcer is $8,000, that of an infected ulcer is $17,000, and that of a major amputation is $45,000. The excess cost attributed to foot ulcers and their sequelae averaged $27,987 per patient for a 2-year period following ulcer presentation (American Diabetes Association; US Department of Health and Human Services; Diabetes Care; Journal of Clinical investigations; JAMA 293:217-228, 2005; Diabetes Care 22:157-162, 1999).

Free blood flow to a site of injury provides access for signaling molecules and nutrients. Regulation of proliferation and remodelling of collagen formation requires coordination of molecular processes (e.g. protease and protease inhibitor balance). Immune and inflammatory response ensure bacteria and debris are phagocytosed and removed prevent infection (J Invest Dermatol. 2007 May; 127(5): 1018-29). If untreated, a diabetic ulcer can progress from a small irritated but unbroken skin patch to a potentially life-threatening wound involving extensive tissue death and infection. Treatment of the diabetic skin ulcer may include drying out the wound, debriding (excising) the dead tissue, and administering systemic antibiotics. (American College of Foot and Ankle Surgeons; Medscape website; Clinical Diabetes Spring 2009 vol. 27 no. 2 52-58).

In regard to the use of platelet lysate in cosmetics it is well known that healthy skin requires tight coordination at the physiological, cellular and molecular levels. Three critical functions required for sustained healthy skin include functioning connective tissue cells, intact skin extracellular matrix (ECM), and tight molecular regulation of the proliferation and remodeling process.

The process to form new tissue requires the action and balance of a number of factors including proteases, tissue inhibitors, and pro- and anti-inflammatory molecules. Coordinated regulation of these factors ensures permanent collagen tissue is being generated while the temporary scaffold is degraded.

Functioning Connective Tissue Cells

Cells within the skin, such as fibroblasts and keratinocytes, are required to synthesize, maintain and provide the extracellular matrix (ECM) that functions as the structural framework of the skin. It is especially important for fibroblasts, which produce the majority of collagen in the skin, to remain healthy and elastic [1]. Platelet and growth factor based solutions enhance wound healing by increasing local concentration of beneficial factors [2, 3]. Current therapies are invasive or minimally accelerate the process of wound healing. An advanced dressing such as hydrocolloid gel have limited improvement over traditional non-adherent gauze in the treatment of diabetic ulcers [6]. Technological breakthroughs in wound healing have also been limited over the last 15 years, with little improvement regarding patient quality-adjusted life year (QALY) outcomes [7].

In healthy skin, intact type I collagen fibrils in the dermis provide mechanical stability and attachment sites for fibroblasts. Receptors (integrins) on the surface of fibroblasts attach to collagen (and other proteins in the dermal extracellular matrix). Cytoskeletal machinery (actin-myosin microfilaments, not shown) within fibroblasts pulls on the intact collagen matrix, which in turn offers mechanical resistance. Dynamic mechanical tension that is created promotes assembly of intracellular scaffolding (microtubules/intermediate filaments, not shown), which pushes outward to cause fibroblasts to stretch. This stretch is required for fibroblasts to produce normal levels of collagen and proteases.

Intact Skin Extracellular Matrix (ECM)

A healthy balance of intact collagen (the most abundant protein in ECM), elastin, hyaluronic acid, proteoglycans, fibronectin, and laminin are necessary for healthy, wrinkle-free skin. These components create a scaffold to support the skin and give it an evenly distributed texture [8].

Tight Molecular Regulation of the Proliferation and Remodelling Process.

Forming new tissue requires the action and balance of a number of factors including proteases, tissue inhibitors, and pro- and anti-inflammatory molecules. Coordinated regulation of these factors ensures permanent collagen tissue is being generated; damaged molecules are cleaved and cleared, and overall health of the connective tissue [9].

All fibrillar collagens consist of three polypeptide chains wound around each other in a triple helical configuration. The soluble triple helix, which is termed procollagen, is assembled inside fibroblasts. Procollagen is secreted from fibroblasts, and the peptide ends are removed by two enzymes in the extracellular space [10]. Removal of the ends produces collagen, which spontaneously assembles (i.e., matures) into large fibres that are enzymatically cross-linked. This cross-linking is necessary for normal structural support [11]. Type I collagen undergoes natural breakdown by enzymatic degradation; however, this degradation in human skin is exceedingly slow [12]. Humans express only four enzymes that are capable of initiating breakdown of type I collagen [13].

These collagenases are members of a family of matrix protein-degrading enzymes, referred to as matrix metalloproteinases (MMPs) [14]. MMPs are responsible for physiological degradation of various extracellular matrix proteins [12]. Of the four collagenases that are expressed in humans, only interstitial collagenase (MMP-1) is involved in normal turnover of skin collagen [14]. In healthy young skin, MMP-1 expression is exceedingly low, near the limit of detection by the most sensitive measurement methods.

Once cleaved by MMP-1, collagen unravels, then un-raveled collagen, called gelatin, then undergoes further degradation by other members of the MMP family, called gelatinases. These gelatinases are also expressed at very low levels in normal skin [14, 15]. In addition, skin expresses natural inhibitors of these MMPs. These tissue inhibitors of matrix metalloproteinases (TIMPs) further act to retard collagen breakdown. Thus, type I collagen in human skin is very stable, requiring approximately 30 years on average to undergo replacement [1, 12].

Wrinkles

Wrinkles are caused by habitual facial expressions, aging, sun damage, smoking, poor hydration and various other factors. Under stress, fibroblasts produce less ECM molecules and more molecules which break down the existing matrix. This leads to further malfunctioning of the connective tissue cells in a feedback loop.

Malfunctioning of Connective Tissue Cells

A delicate relationship exists between mechanical tension, collagen synthesis and collagen fragmentation by collagenase (COLase) in human skin. In aged human skin, attachments of fibroblasts to integrins are lost and fragmented collagen fibrils fail to provide sufficient mechanical stability to maintain normal mechanical tension. Reduced mechanical tension causes fibroblasts to collapse, and collapsed fibroblasts produce less procollagen and more collagenase (COLase). Reduced collagen production and increased collagenase-catalysed collagen fragmentation result in further reduction of mechanical tension, thereby causing continual loss of collagen [1].

Breakdown of the Existing ECM

The existing ECM molecules, especially collagen fibres, are broken down through physical, chemical, or proteolytic damage, leaving collagen and other molecular fragments throughout the ECM.

The slow rate of type I collagen turnover allows accumulation of age-dependent modifications that impair its functions. These alterations include formation of new cross-links derived from sugars [14]. Importantly, these crosslinks are not able to be efficiently broken down and removed during the slow normal process of MMP-mediated turnover, causing accumulation of fragmented collagen within the extracellular matrix as skin ages [15, 16]. Cross-links prevent complete removal of collagen fragments. The fragments cannot be repaired or incorporated into newly made collagen fibrils, and therefore cause defects in the three dimensional collagen matrixes. These defects impair the structural and mechanical integrity of the dermis and thereby deleteriously alter its function. Accumulation of fragmented collagen lies at the heart of age-related changes in the appearance of human skin [1].

Deregulated Molecular Signaling

Collapsed fibroblasts and degraded ECM disproportionately increase the concentration of matrix metalloproteases to tissue inhibitors of metalloproteases (TIMP) at the wrinkle site, impeding tissue regeneration [1, 10-20].

Reactive oxygen species (ROS), a by-product of both environmentally induced and intrinsic aging, cause a cascade of biochemical reactions within the skin, which results in the production of matrix metalloproteinases (MMPs) and proinflammatory cytokines. MMPs, secreted by fibroblasts and keratinocytes, decrease collagen formation and enhance collagen degradation, contributing to the breakdown of the dermal matrix [19].

Current Wrinkle Therapies

Current treatments on the market fail, they do not recreate youthful appearance with lasting results. They aim to treat the symptoms of wrinkles without addressing the root causes. Toxins temporarily relax muscles in the face that stretch the skin, but does not repair the underlying extracellular matrix. Botox® and Dysport® can result in 'frozen face,' with problems swallowing, speaking, and breathing. Fillers (such as hyaluronic acid, collagen, poly-L-lactic acid, and hydroxylapatite) 'fill the gaps' for a short period, but does not restore skin to normal physiology or prevent the degenerative cycle.

Technological breakthroughs in cosmetics have been limited over the last 30 years, with sporadic advancements over the last decade. First and second generation injectable therapies have a quick time to onset, but a limited duration of effect.

Platelet Lysate Therapies

There are several long standing issues affecting the wide spread adaptation and use of platelet lysate (PL) in the clinic. The main issues have been, but are not limited to the following: donor derived samples run the risk of contamination during processing; platelet quality varies from patient to patient in terms of count and ability to secrete beneficial growth factors making the preparations inconsistent; there is a need for platelet quantitation in physician office kits; therapeutic preparation introduces high patient-by-patient variability affecting efficacy due to intrinsic differences in platelet count; current methods are inconvenient, clinicians must centrifuge blood to isolate platelets from blood, and the variability of this process, which can last between 25-30 minutes, again introduces errors; and the current processes are not cost-effective with an estimated cost of $130 per treatment (Plateltex). The invention is a non-obvious solution to these long standing and persistent problems.

DESCRIPTION OF THE FIGURES

FIGS. 2 and 3 show that the invention provides a cost-effective, differentiated product that is convenient, consistent and cGMP compliant FIGS. 4 to 7 show that the solves the long standing and persistent need to provide a consistent wound care product that is quality controlled, convenient to use and cost effective.

SUMMARY OF THE INVENTION

Figure 1:
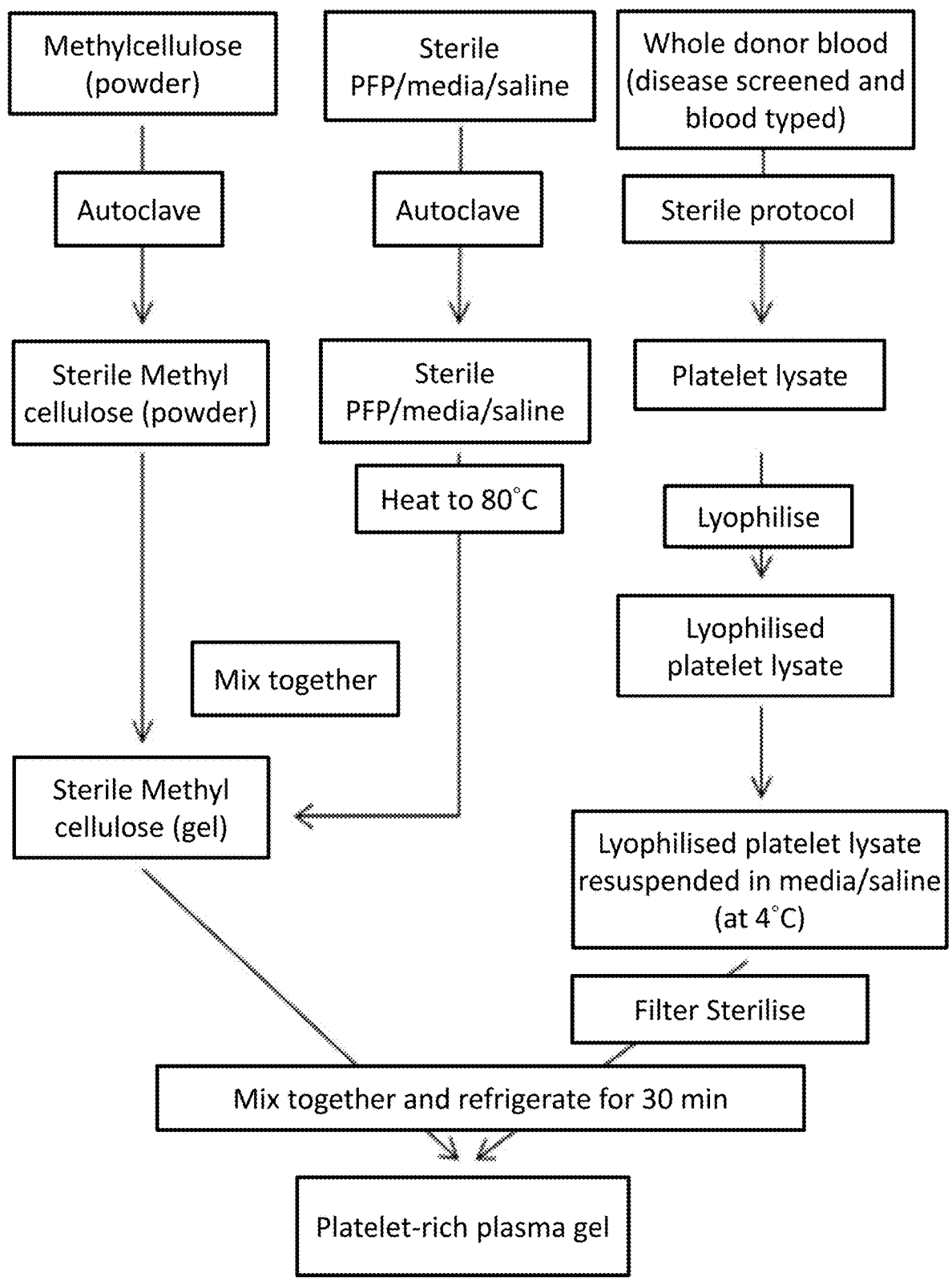
FIG. 1 shows a flowchart of the protocol used to produce a platelet lystate of the invention and a pharmaceutical composition of the invention.
Figure 3:
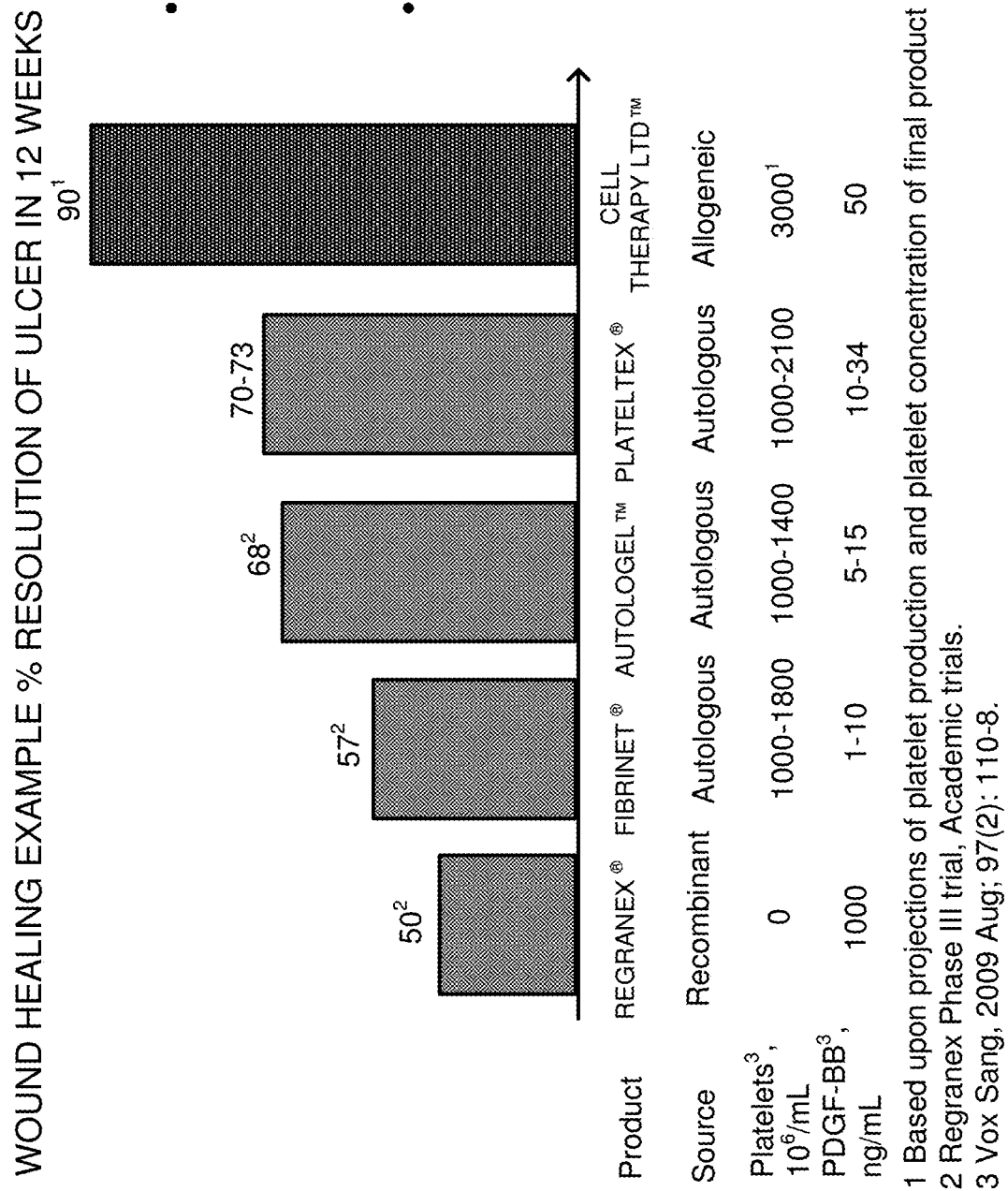
Figure 4:
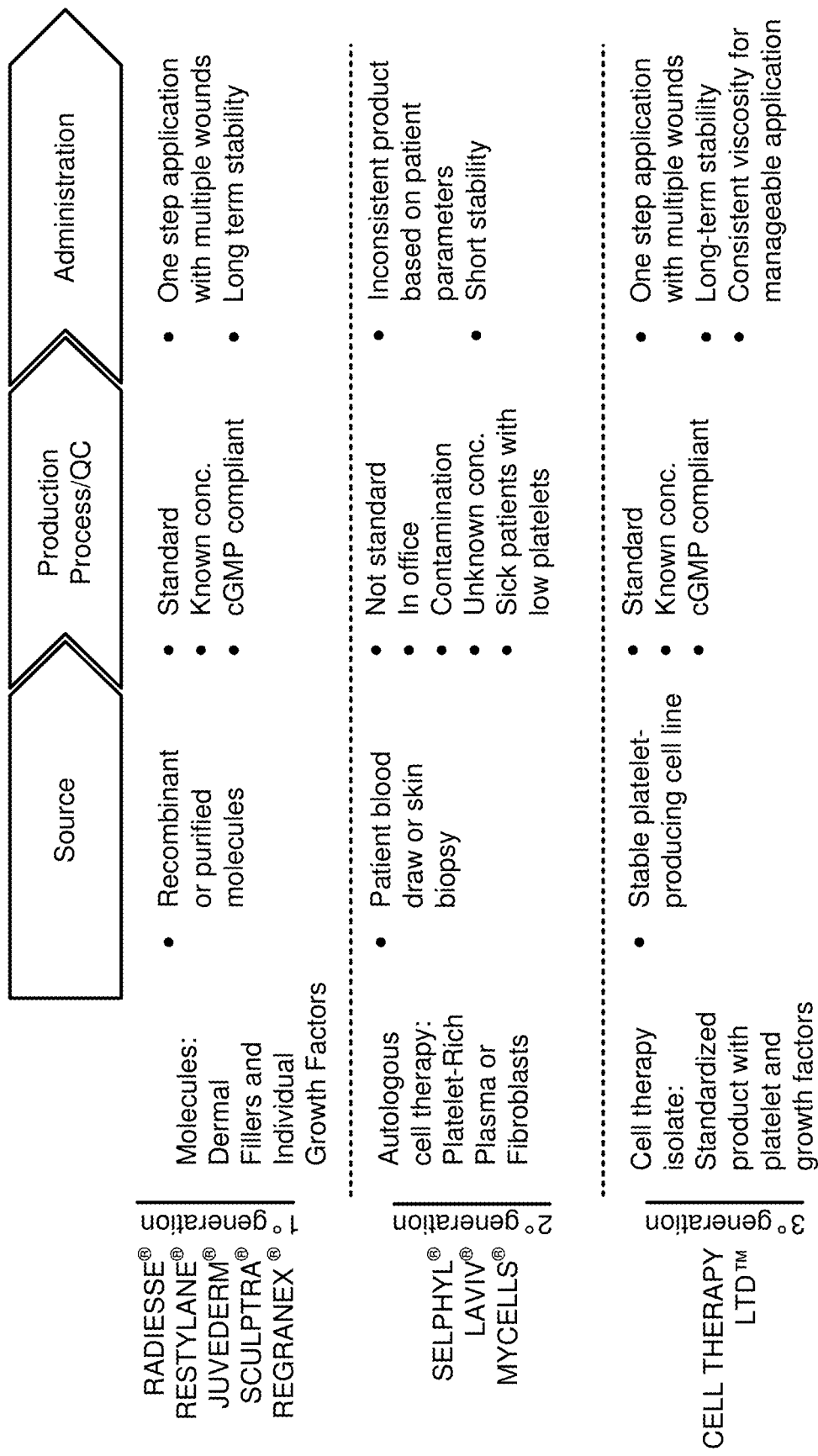
Figure 6:
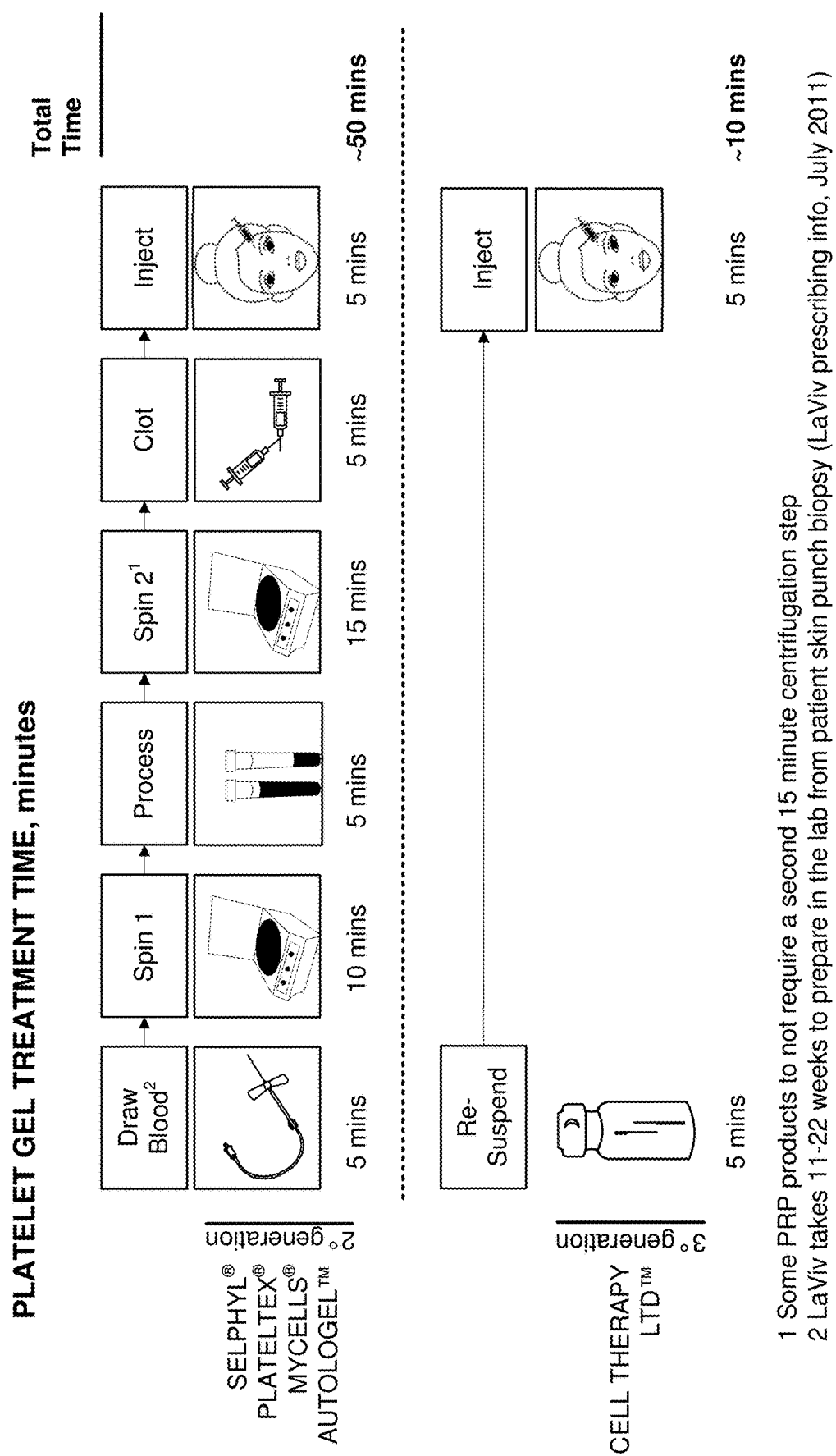
Figure 7:
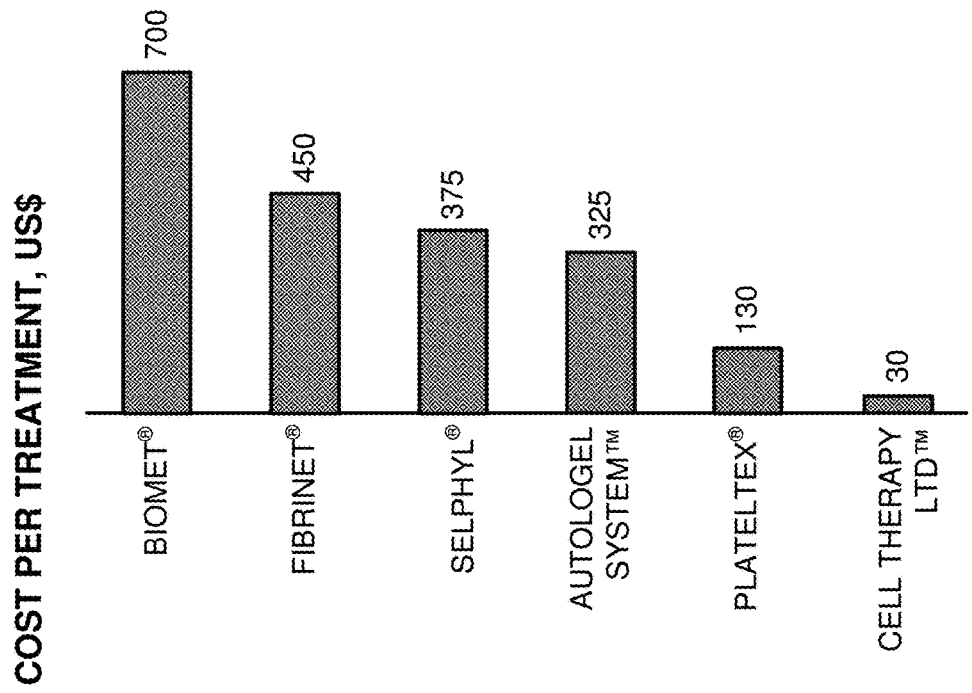

The invention provides a pharmaceutical composition comprising a platelet lysate. These may be therapeutically applied to wounds, such as ulcerated wounds, anal fissures, vaginal atrophy or wrinkles.

The inventors have also devised a more efficient way of lysing platelets such they release their growth factors into solution as a platelet lysate. The novel platelet lysate may itself be used as a therapeutic or may be formulated into a pharmaceutical composition of the invention.

The composition or lysate of the invention may be lyophilised to produce a stabilized, freeze-dried powder that contains these growth factors and which can be used for therapeutic application in wound healing, but also other therapeutic applications in which there is an increased need for delivery of natural growth factors.

The invention provides a pharmaceutical composition comprising (a) a therapeutic platelet lysate, (b) at least one pharmaceutically acceptable polymer and (c) at least one pharmaceutically acceptable positively charged chemical species selected from the group consisting of lysine, arginine, histidine, aspartic acid, glutamic acid, alanine, methionine, proline, serine, asparagine, cysteine, polyamino acids, protamine, aminoguanidine, zinc ions and magnesium ions, wherein the composition is an aqueous gel having a viscosity in the range of 1000 to 500,000 mPa·s (cps) at room temperature.

The invention also provides:
a method of producing a platelet lysate comprising subjecting a population of platelets to at least one freeze-thaw cycle, wherein the freeze portion of each cycle is carried out at a temperature lower than or equal to −78° C.;

a method of producing platelet lysate comprising subjecting a population of platelets to mechanical homogenisation ('waring blender'), liquid homogenization, sonication, freeze-thaw using alcohol and dry ice or other means, mechanical grinding in liquid nitrogen at >75%, but typically >90%, lysis to release growth factors from platelets and alpha granules into solution whereas rotating blades grind and disperse cells and tissues; cell or tissue suspensions are sheared by forcing them through a narrow space; high frequency sound waves shear cells; repeated cycles of freezing and thawing disrupt cells through ice crystal formation; grinding tissue, frozen in liquid nitrogen wherein lysis releases growth factors from platelets and alpha granules into solution;

a platelet lysate produced using a method of the invention;

a pharmaceutical composition of the invention or a platelet lysate of the invention for use in treating a wound, an anal fissure, vaginal atrophy or a wrinkle in a patient in need thereof;

a method of treating a wound, an anal fissure, vaginal atrophy or a wrinkle in a patient in need thereof, comprising administering to the patient a therapeutically effective amount of a pharmaceutical composition of the invention or a platelet lysate of the invention;

a method of producing a pharmaceutical composition of the invention comprising mixing a platelet lysate with at least one pharmaceutically acceptable polymer and at least one pharmaceutically acceptable positively charged chemical species such that the resulting composition is an aqueous gel having a viscosity in the range of 1000 to 500,000 mPa·s (cps) at room temperature; and a method of producing a pharmaceutical composition of the invention comprising (a) producing a platelet lysate using a method according to any one of claims 14 to 20 and (b) mixing the platelet lysate with at least one pharmaceutically acceptable polymer and at least one pharmaceutically acceptable positively charged chemical species such that the resulting composition is an aqueous gel having a viscosity in the range of 1000 to 500,000 mPa·s (cps) at room temperature.

DETAILED DESCRIPTION OF THE INVENTION

Invention Details

The pharmaceutical composition of the invention or the platelet lysate of the invention will be applied, and all components will undergo rigorous testing to ensure that our product is safe and effective for the patient. These processes include platelet screening and methods to allow for the production of sterile platelet gel. The invention implements processes which are safe, effective, and sterile. In a preferred embodiment, sterile platelet lysate is mixed with sterile methylcellulose gel to create a therapeutic platelet composition of the invention. A flowchart of the protocol of the invention can be found in FIG. 1.

Effectiveness of Pharmaceutical Composition of the Invention for Wrinkles

The invention provides a regenerative therapy that directly addresses each of the problems associated with wrinkles and enhances the skin and the underlying scaffold. Treatment with a pharmaceutical composition of the invention or a platelet lysate of the invention reverses damaged skin's degenerative cycle to the healthy physiology found in normal skin. The pharmaceutical composition of the invention or platelet lysate of the invention works by rebalancing cells within the connective tissues, equilibrating molecular signalling, and restoring extracellular matrix. The natural healing and tissue regeneration process leads to increased collagen synthesis, regeneration of the collagen extracellular matrix and proliferation of the fibroblasts within the matrix.

Rebalanced Cells within the Connective Tissues

Since the pharmaceutical composition of the invention is derived from platelets, it typically comprises various growth factors which are derived from platelets and promote cell growth. The pharmaceutical composition of the invention or the platelet lysate of the invention typically comprises one or more of, preferably all of, the following growth factors: PDGF, VEGF, FGF, EGF, TGF, especially TGF-β, and CTGF. The composition preferably comprises 2, 3, 4, 5 or 6 of these growth factors.

Platelet-derived growth factor (PDGF) promotes cell growth and generation, repair of blood vessels and collagen production. Vascular endothelial growth factor (VEGF) promotes growth and generation of vascular endothelial cells. Fibroblast growth factor (FGF) promotes tissue repair, cell growth, collagen production and hyaluronic acid production. Epithelial growth factor (EGF) promotes epithelial cell growth, angiogenesis and wound healing. Transforming growth factor (TGF), especially TGF-β, promotes growth and neogenesis of epithelial cells and wound healing. Connective tissue growth factor (CTGF) promotes wound repair.

The pharmaceutical composition of the invention or the platelet lysate of the invention therefore promotes the formation of new fibroblasts. These new fibroblasts start elastic and healthy, producing new collagen and less metalloproteases. The restoration of fibroblasts (the major cell in synthesizing, maintaining and providing the structural framework) results in healthier, restored skin [1].

PDGF has also been show to increase fibroblast motility, allowing fibroblasts to relocate to the site of administration.

Restored Extracellular Matrix (ECM)

Natural growth factors found in the alpha-granules of platelets (such as PDGF, VEGF, FGF, EGF, and TGF) promote collagen and hyaluronic acid production, tissue repair, growth and regeneration of endothelial cells and epithelial cells, and new blood vessel formation (which restores oxygen and removes undesired molecules). All of these factors help to regenerate wrinkled and damaged ECM back to its healthy state. Each of these growth factors plays a role within skin regeneration and restoration, both individually and additively in concert with each other. Treatments that stimulate the production of new, non-fragmented collagen will provide substantial improvement to the appearance and health of aged [1].

Equilibrated Molecular Signalling

Application of platelet lysate under the wrinkle provides a concentrated dose of TIMP protein to address the metalloprotease imbalance, prevents the further degradation of ECM, and increases the speed of skin regeneration. Direct application of platelet lysate to skin provides concentrated dose of TIMP protein to address the metalloprotease imbalance, supporting collagen tissue proliferation and remodelling. Platelets contain for example TIMP-2 which inhibits most MMPs, but preferentially inhibits MMP-2 and MMP-9 [20]. The pharmaceutical composition of the invention or the platelet lysate of the invention typically comprises TIMP metallopeptidase inhibitor 2 (TIMP-2).

Advantages of the Invention

The pharmaceutical composition of the invention or the platelet lysate of the invention will be easily adapted for the chronic wound healing markets and conveys the following advantages over platelet rich plasma and other autologous regenerative cell therapies.

1. Production

In-house, scaled-up cGMP compliant in-vitro platelet production platform to deliver high yields of safe, pure and active platelets.

2. Formulation

Platelets are lysed to release important growth factors. Lysate is concentrated to standard efficacious therapeutic dose and freeze-dried for long term storage at refrigerated temperature. QC testing on artificial skin assay ensures consistent, high concentration of growth factors in every batch and no inter-patient variability seen with autologous platelet rich plasma.

3. Administration

Efficient one-step processes of (a) administering a pharmaceutical composition of the invention or a platelet lysate of the invention, (b) rehydrating a freeze-dried platelet lysate of the invention, (c) mixing a freeze-dried platelet lysate of the invention with polymer gelling factor or (d) rehydrating a pharmaceutical composition of the invention simplifies current process for physicians in the clinic and standardizes patient dosing.

Processing for current platelet rich plasma therapy includes spinning blood and isolating un-concentrated, un-characterized plasma, which varies by patient on growth factor concentration. Unlike other dermal stimulators (e.g., poly-L-lactic acid), platelet therapy produces its effect rapidly. It is reproducible and easy to use.

Additional advantages are shown in Table 1 below.

Platelet therapies are a natural, sustained solution, while known products are unnatural and temporary, the pharmaceutical composition of the invention and platelet lysate of the invention provide a better solution to patients, with fewer visits and cost-savings. Unlike known products, the pharmaceutical composition of the invention and platelet lysate of the invention standardize the concentration of platelets and growth factors, leading to consistent results.

Additionally, the therapeutic composition solves hurdles for providing a consistent dermal regeneration product that is quality controlled, convenient to use and cost effective.

PRODUCTION: The composition of the invention is a cGMP compliant, standardized product that will ensure a consistent dermal regeneration outcome.

USABILITY: The composition of the invention is a one-step application platelet lysate formulation and will save significant time for the physician.

COST: The composition of the invention will deliver dermal regeneration at a cost-effective price when compared with other platelet-rich plasma therapies.

Other non-obvious solution to the problem to be solved are there are no other commercial platelet lysate/methylcellulose gels on the market and there are no other platelet lysate/methylcellulose gels in the literature.

Diabetic Ulcers

Diabetic patients often suffer from peripheral arterial disease that constricts blood flow, which restricts access of signaling molecules and nutrients to the wound site. High concentration of cytokines increase the concentration of metalloproteases to inhibitors at the wound site, impeding normal tissue regeneration. Poor activation of immune-modulatory factors combined with low levels of bactericidal nitric oxide increases probability and severity of infections [21]. While the exact process of wound healing is still not fully understood, it is known that platelets secrete a subset of factors critical to the process. Factors important for wound healing are naturally secreted by platelets, macrophages and fibroblasts. PDGF, EGF and TGF are considered critical factors in the process of wound healing. Additional factors play important role and are secreted by macrophages and fibroblasts recruited to wound site by platelets. Skin is presumably the organ most subject to injury. Skin repair is a complex process that can be divided in 4 phases usually described as inflammation, granulation tissue formation, and epithelialization and remodelling of the connective tissue matrix. Each of these phases is complex in itself, and it is clear that for good wound healing, the processes must occur successively and in coordination. Good wound healing can be defined as restoration of the skin, including the dermal and epidermal part, in such a way that the resulting scar tissue maximally resembles the unwounded skin structurally, histologically, functionally, and aesthetically obviously, such scar tissue is different from a hypertrophic scar or keloid.

For purposes of clarity a simplified description of the composition of human skin is given below. The upper part is composed of the epidermis, which contains mostly epithelial cells, some. Five different layers are found in the epidermis. The base of the epidermis, i.e., in the stratum basal, is attached to the dermis via the basement membrane. The dermis is composed of connective tissue, including fibroblasts and other connective tissue cells, and connective tissue matrix substances. Blood vessels, nerves, sensory organs, sweat glands, sebaceous glands, and hair follicles are present in the dermis. Clinical experiments have demon-

TABLE 1

Advantages of the therapeutic composition of the invention (labeled 4$^{th}$ generation) vs. previous generation products
Table shows major advantages to CTL's fourth generation platelet-rich plasma gel

| Generation | Product | Example | Price | Clinical Convenience | Contamination Risk | Unwanted Impurities | Potency | Long-term Stability | # of Growth Factors | Use with sickly[2] patient |
|---|---|---|---|---|---|---|---|---|---|---|
| 1$^{st}$ | Manufactured growth factor | Regranex | ✓ | ✓ | ✓ | ✓ | ✗ | ✓ | ✗ | ✓ |
| 2$^{nd}$ | Autologous (Self) platelet gel | Autologel | ✗ | ✗ | ✗ | ✗ | ✗[1] | ✗ | ✗[1] | ✗ |
| 3$^{rd}$ | Allogenic (Donor) platelet gel | Academic Trials | ✗ | ✓ | ✓ | ✗ | ✓ | ✗ | ✓ | ✓ |
| 4$^{th}$ | Allogenic (Donor) platelet gel with methylcellulose | CTL | ✓ | ✓ | ✓ | ✓ | ✓ | ✓ | ✓ | ✓ |

[1]Variable by patient
[2]Abnormal blood or platelet physiology strated that application of platelet lysate preparations induces wound healing in chronic wounds such as ulcers and in burns.

Diabetic ulcers are a result of neuropathy and decreased circulation in the lower limbs of the diabetic patient. These difficult to heal wounds form a vast amount of exudate that currently is being managed by absorbing the majority in specific wound dressings. Exudate contains a large variety of proteins and cells. One of these proteins is thrombin (current hypothesis, needs to be confirmed) a component of the coagulation cascade which activates platelets. Platelets are small cells in the blood which form blood clots upon activation and release their growth factor content. They are activated by tissue damage and the blood clot prevents further bleeding. The growth factors promote regeneration and repair of the damaged tissue. The wound healing capacity of platelets has tried to be captured by many researchers in a wide variety of formulations such as platelet-rich plasma, platelet lysate, platelet gel and platelet. These products are prepared by in vitro activated platelets which are then prepared into a suitable formulation and applied to the wound.

The therapeutic platelet concentration has been described to be $1 \times 10^9$ platelets per ml, which we achieve by isolating and concentrating the platelets through centrifugation. The ideal concentration needs to be determined through clinical evaluations, but is likely to range from the concentration in platelet-rich plasma which is roughly the double of that in peripheral blood (i.e. $4 \times 10^8$ platelets/ml if the patient's blood level is $2 \times 10^8$ platelets/ml), to $2 \times 10^9$ platelets/ml. The Gold Standard has been to store isolated platelets at room temperature whilst they agitate until they are processed (standard guidelines followed at the Welsh Blood Service).

Platelet Lysate

Platelet lysate, PL, has been shown to have a positive influence on wound healing. A therapeutic platelet lysate is a platelet lysate that is suitable for therapy. The platelet lysate of the invention or the platelet lysate used in the pharmaceutical composition of the invention typically comprises one or more of, preferably all of, PDGF, VEGF, FGF, EGF, and TGF as described above. It also typically comprises TIMP-2.

Lysis of platelets can be accomplished through chemical means (i.e. CaCl2), osmotic means (use of distilled H2O), or through freezing/thawing procedures. Platelet lysate for use in the invention can also be derived from whole blood and can be prepared as described in U.S. Pat. No. 5,198,357 [22], which is incorporated by reference herein.

Previously, PL has been prepared through freeze-thaw cycles in varying temperatures ranging from −20 to −80 degrees, by rarely using more than 1 cycle. Our data have shown that the number of whole platelets is only moderately affected by a freeze-thaw cycle in −80/+37 degrees. In fact, in a comparison of −20, −80 and liquid nitrogen freezing, only liquid nitrogen was able to achieve 90% lysis whereas −20 and −80 resulted in 80% and 50% lysis, respectively. Notable however is that the experiment above contained 3 freeze-thaw cycles and thus shows that the preparation of PL in current literature using −80 degrees in one freeze-thaw can only achieve about 20% lysis. Liquid nitrogen also holds the advantage of enabling 3 or more freeze-thaw cycles to be performed within an hour, and is thus a highly suitable method for the clinical setting. Furthermore, liquid nitrogen facilitates process standardization as the liquid form of the gas always is −196° C. whereas freezers can differ in temperature over time, especially when there are multiple users who open the door frequently naturally standardization is of particular importance when preparing a product for use in the clinic.

The invention provides a method of producing a platelet lysate (PL) comprising subjecting a population of platelets to at least one freeze-thaw cycle, wherein the freeze portion of each cycle is carried out at a temperature lower than or equal to −78° C. The method may involve any number of freeze-thaw cycles, such as 1, 2, 3, 4, 5, 6, 7, 8, 9, 10, 15, 20, 25, 30 or more. The method preferably comprises subjecting the population of platelets to 5 or fewer freeze-thaw cycles, such as 4 or fewer freeze-thaw cycles, 3 or fewer freeze-thaw cycles or 2 or fewer freeze-thaw cycles. The method more preferably comprises subjecting the population of platelets to only one freeze-thaw cycle, only two freeze-thaw cycles, only three freeze-thaw cycles or only four freeze-thaw cycles.

The thaw temperature in each cycle may be any temperature that thaws the platelet composition, such from about 5° C. to about 50° C., such as from about 10° C. to about 45° C. or from about 20° C. to about 40° C. The thaw temperature in each cycle is typically about 37° C.

The freeze temperature in each cycle is preferably lower than or equal to about −79° C., lower than or equal to about −80° C., lower than or equal to about −81° C., lower than or equal to about −82° C., lower than or equal to about −83° C., lower than or equal to about −84° C., lower than or equal to about −85° C., lower than or equal to about −86° C., lower than or equal to about −87° C., lower than or equal to about −88° C., lower than or equal to about −89° C., lower than or equal to about −90° C., lower than or equal to about −100° C., lower than or equal to about −110° C., lower than or equal to about −120° C., lower than or equal to about −130° C., lower than or equal to about −140° C., lower than or equal to about −150° C., lower than or equal to about −160° C., lower than or equal to about −170° C., lower than or equal to about −180° C., lower than or equal to about −190° C. or about −196° C.

The freeze and thaw temperatures in different cycles of the same method are typically the same.

In a preferred embodiment, liquid nitrogen is used as a cryogenic means in each freeze cycle. Immersion in liquid nitrogen in the freeze portion of each cycle typically results in 95% or more lysis of platelets resulting in greater growth factor release and improved function in cell growth, repair and regeneration measurable by, but not limited to, fibroblast and PGDF assay.

The invention also provides a platelet lysate produced using a method of the invention. This platelet lysate differs from known lysate because it results from greater than about 80% lysis of the platelets, such as greater than about 85% or greater than about 90% lysis of the platelets. It therefore comprises more growth factors and an improved function in cell growth, repair and regeneration measurable by, but not limited to, fibroblast and PGDF assay.

The platelet lysate is present in the pharmaceutical composition of the invention at a concentration within the range of from about 0.1 µg to about 1,000 µg per gram of composition, such as from about 0.2 µg to about 750 µg per gram of composition, from about 0.5 µg to about 500 µg per gram of composition, from about 1 µg to about 250 µg per gram of composition, from about 2 µg to about 200 µg per gram of composition or from about 10 µg to about 100 µg per gram of composition.

The platelet lysate of the invention or the platelet lysate used in the pharmaceutical composition of the invention may be derived from the platelets of any mammal. The mammal is preferably a human. However, it may be non-human. Suitable non-human animals include, but are not limited to, primates, such as marmosets or monkeys, commercially farmed animals, such as horses, cows, sheeps, goats, alpacas, guanacos, deer or pigs, pets, such as dogs, cats, mice, rats, guinea pigs, ferrets, gerbils or hamsters or wild animals such as badgers or deer.

Pharmaceutically Acceptable Polymer

The pharmaceutical composition of the invention comprises at least one pharmaceutically acceptable polymer. The composition may comprise any number of pharmaceutically acceptable polymers, such as 1, 2, 3, 4, 5, 10 or more.

A polymer is pharmaceutically acceptable if it suitable for use in therapy. The polymer is preferably suitable for topical administration to a wound, such as any of the wounds discussed herein, an anal fissure, vaginal atrophy or a wrinkle.

Pharmaceutically acceptable polymers are well known in the art. Any such polymers may be used in accordance with the invention.

The polymer concentration is preferably from about 15% (w/w) to about 30% (w/w), such as from about 17% (w/w) to about 25% (w/w) or from about 20% (w/w) to about 23% (w/w).

The polymer is preferably a cellulose polymer. Suitable cellulose polymers are know in the art. The cellulose polymer is carboxymethylcellulose, hydroxypropylmethylcellulose or methylcellulose. The cellulose polymer concentration is preferably from about 1.5% (w/w) to about 4.0% (w/w), such as from about 2.0% (w/w) to about 3.0% (w/w). The cellulose polymer preferably has a molecular weight of from about 450,000 to about 4,000,000, such as from about 500,000 to about 3,500,000, from about 500,000 to about 3,000,000 or from about 750,000 to about 2,500,000 or from about 1000,000 to about 2,000,000.

The polymer is preferably a pluronic acid, optionally Pluronic F-127.

Pharmaceutically Acceptable Positively Charged Chemical Species

The pharmaceutical composition of the invention comprises at least one pharmaceutically acceptable positively charged chemical species selected from the group consisting of lysine, arginine, histidine, aspartic acid, glutamic acid, alanine, methionine, proline, serine, asparagine, cysteine, polyamino acids, protamine, aminoguanidine, zinc ions and magnesium ions.

A species is pharmaceutically acceptable if it suitable for use in therapy. The species is preferably suitable for topical administration to a wound, such as any of the wounds discussed herein, an anal fissure, vaginal atrophy or a wrinkle.

The composition may comprise any number of pharmaceutically acceptable species, such as 1, 2, 3, 4, 5, 6, 7, 8, 9, 10, 11, 12, 13, 14, 15 or 16 of the listed species.

The concentration of the charged species is preferably within the range of from about 0.1% (w/w) to about 3.0% (w/w), such as from about 0.2% (w/w) to about 2.5% (w/w), from about 0.5% (w/w) to about 2.0% (w/w) or from about 1.0% (w/w) to about 1.5% (w/w).

Viscosity

The pharmaceutical composition of the invention is an aqueous gel. The polymer(s) within the composition form a network within which water molecules are dispersed. The pharmaceutical composition of the invention is preferably a hydrogel.

The aqueous gel has a viscosity in the range of from about 1000 to about 500,000 micropascal-second (mPa·s) (also known as centipoises; cps) at room temperature. Viscosity is a measure of the resistance of the gel to being deformed by either shear stress or tensile stress. Viscosity can be measured using any method known in the art. Suitable methods include, but are not limited to, using a viscometer or a rheometer.

Room temperature is typically from about 18° C. to about 25° C., such as from about 19° C. to about 24° C. or from about 20° C. to about 23° C. or from about 21° C. to about 22° C. Room temperature is preferably any of 18° C., 19° C., 20° C., 21° C., 22° C., 23° C., 24° C. and 25° C. Viscosity is most preferably measured at 25° C.

The gel preferably has a viscosity in the range of from about 1000 to about 500,000 mPa·s at room temperature, such as from about 1500 to about 450,000 mPa·s at room temperature, from about 2000 to about 400,000 mPa·s at room temperature, from about 2500 to about 350,000 mPa·s at room temperature, from about 5000 to about 300,000 mPa·s at room temperature, from about 10,000 to about 250,000 mPa·s at room temperature, from about 50,000 to about 200,000 mPa·s at room temperature or from about 50,000 to about 150,000 mPa·s at room temperature.

The gel most preferably has a viscosity in the range of from about 50,000 to about 150,000 mPa·s(cps) at 25° C.

Preservatives

The pharmaceutical composition of the invention or the platelet lysate of the invention may further comprise one or more preservatives. Suitable preservatives are known in the art. Suitable preservatives include, but are not limited to, methylparaben, propylparaben and m-cresol.

Additional Growth Factors

In addition to the growth factors derived from the platelet lysate, the pharmaceutical composition of the invention or the platelet lysate of the invention may further comprise one or more additional or exogenous growth factors. Any growth factor may be present.

Additional amounts of one or more of, preferably all of, PDGF, VEGF, FGF, EGF, TGF, especially TGF-β, and CTGF may be added to the pharmaceutical composition of the invention or the platelet lysate of the invention.

The pharmaceutical composition of the invention or the platelet lysate of the invention may further comprise one or more antibiotics, analgesics or debriding agents. The pharmaceutical composition of the invention or the platelet lysate of the invention may further comprise silver Cells The pharmaceutical composition of the invention or platelet lysate of the invention may further comprise one or more stem cells. These can assist with the wound healing nature of the composition. The stem cells may be mesenchymal stem cells (MSC) or hematopoietic stem cells.

The pharmaceutical composition of the invention or platelet lysate of the invention may further comprise one or more progenitor cells, mononuclear cells or endothelial progenitor cells.

The pharmaceutical composition of the invention or platelet lysate of the invention may further comprise a progenitor cell of the mesodermal lineage as described in International Application No. PCT/GB2012/051600. These cells express detectable levels of CD29, CD44, CD73, CD90, CD105 and CD271 and do not express detectable levels of CD14, CD34 and CD45.

Any cells present in the composition or lysate are preferably autologous. In other words, the cells are preferably derived from the patient to which the cells will be administered. Alternatively, the cells are preferably allogeneic. In other words, the cells are preferably derived from a patient that is immunologically compatible with the patient to which the cells will be administered.

Definitions

The following definitions are provided to facilitate understanding of certain terms used frequently herein and are not meant to limit the scope of the present disclosure.

"Platelet lysate" (aka "platelet released") refers to the combination of natural growth factors contained in platelets that has been released through lysing those platelets.

"Protein," "peptide," and "polypeptide" are used interchangeably to denote an amino acid polymer or a set of two or more interacting or bound amino acid polymers.

"Stem cells" refers to any cell having the characteristic of being unspecialized and able to renew for extended periods of time through cell division and being inducible to become cells with specialized function.

"Lyophilisation" (aka freeze-drying, lyophilisation or cryodesiccation) is a dehydration process typically used to preserve a perishable material or make the material more convenient for transport. Freeze-drying works by freezing the material and then reducing the surrounding pressure to allow the frozen water in the material to sublime directly from the solid phase to the gas phase. Methods for lyophilising compositions are known in the art.

Lyophilisation

Lyophilisation is advantageous in that the resulting substance is easier to store, can be kept in a small place, is easier to handle, can be applied in a formulation (e.g., in a dry powder, an ointment, a suspension, a solution, a gel, a cream or a biocompatible, synthetic or natural solid matrix) chosen according to the circumstances, can be administered at an optimal dose, normally has a longer shelf life, and can easily be screened for the most active preparation. One advantage of lyophilised cell extracts is that the material is readily available exactly at the moment it is needed, in contrast to extract gels.

The invention also provides a platelet lysate produced using a method of the invention wherein the platelet lysate is lyophilised or in a lyophilised form. The invention further relates to extracts of a platelet lysate produced using a method of the invention wherein the platelet lysate is lyophilised or in a lyophilised form. The methods of producing a platelet lysate of the invention may further comprise lyophilising the platelet lysate. Methods suitable for lyophilising the platelet lysate are known in the art.

Such extracts can be formed in a conventional manner. The term "extract" refers to a lysate product obtained from human cell lysate which has retained its healing activity. Such extracts are discussed above. A platelet lysate extract can be prepared, for instance, after lysis and/or disruption of the blood cells followed by lyophilisation as described above.

Such lyophilised compositions can be applied as a dry powder, in an ointment, in a suspension, in a solution, in a gel, in a cream or in a biocompatible, synthetic or natural, solid matrix, chosen according to the circumstances and administered in an optimal dose.

The pharmaceutical composition on the invention may be lyophilised or in a lyophilised form. The methods of producing a pharmaceutical composition of the invention may further comprise lyophilising the pharmaceutical composition. Methods suitable for lyophilising the pharmaceutical composition are known in the art.

Medicaments, Methods and Therapeutic Use

A pharmaceutical composition of the invention or a platelet lysate of the invention may be used in a method of therapy of the human or animal body. Thus, the invention provides a pharmaceutical composition of the invention or a platelet lysate of the invention for use in treating a wound, an anal fissure, vaginal atrophy or a wrinkle in a patient in need thereof.

The invention also provides a method of treating a wound, an anal fissure, vaginal atrophy or a wrinkle in a patient in need thereof, comprising administering to the patient a therapeutically effective amount of a pharmaceutical composition of the invention or a platelet lysate of the invention.

The invention concerns administering to the patient a therapeutically effective amount of a pharmaceutical composition of the invention or a platelet lysate of the invention. A therapeutically effective amount is an amount which ameliorates one or more symptoms of the wound, anal fissure, vaginal atrophy or wrinkle. A therapeutically effective amount is preferably an amount which repairs the wound, anal fissure, vaginal atrophy or wrinkle. Suitable amounts are discussed in more detail below.

The pharmaceutical composition of the invention or the platelet lysate of the invention may be administered to any suitable patient. The patient may be any mammal. The patient is generally a human patient. The patient may be an infant, a juvenile or an adult. The patient is typically known to have wound, an anal fissure, vaginal atrophy or a wrinkle.

The platelets used to prepare pharmaceutical composition of the invention or the platelet lysate of the invention are preferably autologous. In other words, the platelets are preferably derived from the patient to which the pharmaceutical composition of the invention or the platelet lysate of the invention will be administered. Alternatively, the platelets are preferably allogeneic. In other words, the platelets are preferably derived from a patient that is immunologically compatible with the patient to which the pharmaceutical composition of the invention or a platelet lysate of the invention will be administered.

The pharmaceutical composition of the invention or the platelet lysate of the invention used in therapy may comprise one or more stem cells or progenitor cells of the mesodermal lineage as discussed above. It may also comprise additional growth factors as discussed above.

The invention may be used in combination with other means of, and substances for, treating the wound, anal fissure, vaginal atrophy or wrinkle or providing pain relief. In some cases, the pharmaceutical composition of the invention or the platelet lysate of the invention may be administered simultaneously, sequentially or separately with other substances which are intended for repairing the wound, anal fissure, vaginal atrophy or wrinkle or for providing pain relief. The pharmaceutical composition of the invention or a platelet lysate of the invention may be used in combination with existing treatments for wound, anal fissures, vaginal atrophy or wrinkles and may, for example, be simply mixed with such treatments. Thus the invention may be used to increase the efficacy of existing treatments or cosmetics.

Pharmaceutical Compositions and Administration

The pharmaceutical composition of the invention and platelet lysate of the invention may be formulated with pharmaceutically acceptable carriers and/or excipients using routine methods in the pharmaceutical art. The exact nature of a formulation will depend upon several factors including the nature of the composition or lysate and the desired route of administration. Suitable types of formulation are fully described in Remington's Pharmaceutical Sciences, 19th Edition, Mack Publishing Company, Eastern Pennsylvania, USA.

The pharmaceutical composition of the invention or platelet lysate of the invention is typically sterile.

The pharmaceutical composition of the invention or the platelet lysate of the invention may be administered by any route. The pharmaceutical composition of the invention or the platelet lysate of the invention is typically administered topically to the wound, anal fissure, vaginal atrophy or wrinkle.

The pharmaceutical composition of the invention or the platelet lysate of the invention may be prepared together with a physiologically acceptable carrier or diluent. Suitable carriers or excipients are, for example, water, saline, dextrose, glycerol, of the like and combinations thereof. Lyophilised compositions or lysates are typically rehydrated before therapeutic use.

In addition, if desired, the pharmaceutical composition of the invention or the platelet lysate of the invention may contain minor amounts of auxiliary substances such as wetting or emulsifying agents, pH buffering agents, and/or adjuvants which enhance effectiveness. Such agents are known in the art.

The pharmaceutical composition of the invention or the platelet lysate of the invention are administered in a manner compatible with the dosage formulation and in such amount will be therapeutically effective. The quantity to be administered depends on the subject to be treated, capacity of the subject's immune system and the degree repair desired. Precise amounts of required to be administered may depend on the judgment of the practitioner and may be peculiar to each subject.

Any suitable amount of the pharmaceutical composition of the invention or the platelet lysate of the invention may be administered to the subject. For example, an amount sufficient to cover the wound, anal fissure, vaginal atrophy or wrinkle is typically administered. The actual amount administered will therefore depend on the size of the wound, anal fissure, vaginal atrophy or wrinkle. For instance, the amount of the pharmaceutical composition of the invention which is administered may range from about 0.1 g to 100 g, such as from about 0.5 g to about 75 g, from about 1 g to about 50 g, from about 2 g to about 20 g or from about 3 g to 10 g.

The pharmaceutical composition of the invention or the platelet lysate, either of which may be in lyophilised form, may be therapeutically applied to the wound. The processing of the platelets releases the growth factors into solution and the lyophilisation process would produce a stabilized, freeze-dried pharmaceutical powder consisting of these factors. This lyophilised pharmaceutical composition or platelet lysate could be combined with other technologies for effective treatment of clinical wound patients with much greater long term stability at different temperatures. This would circumvent the logistical process of preparation and transfer of the treatment.

One embodiment is a dry, lyophilised pharmaceutical composition of the invention or a dry, lyophilised platelet lysate. When combined with water, just prior to treatment, a gel-like consistency would be formed.

In other embodiments, a pharmaceutical composition of the invention or a platelet lysate of the invention could alternatively be combined with different:

formulation/delivery methods, such as:
Lotion, Shake lotion, Cream, Ointment, Gel, Foam, Transdermal patch, Powder, Solid, Sponge, Tape, Paste, bandage, gauze, syringe, spray
treatments, such as:
Mesenchymal stem cells, hematopoietic stem cells, mononuclear cells, endothelial progenitor cells, mesodermal progenitor cells, antibiotics, analgesics, silver, debriding agents, medical devices
Methods of packaging, such as:
Sterile package, bottle, box, can
Methods of storage
Ideally, room temperature powder; refrigerated or frozen, as necessary The invention still further relates to a pharmaceutical composition containing, as an active substance, an extract as defined above, which is preferably in lyophilised form and which can be used to promote the healing of surface wounds, for example of skin, such as human skin. This pharmaceutical composition preferably comprises the lyophilised extract in a formulation suitable for application onto surface wounds. Such a formulation can be applied directly to a surface wound either as a dry powder or in the form of a gel, a cream, an ointment, a suspension, a solution, or a biocompatible, synthetic or natural solid matrix, any of which can be prepared in a conventional manner, if desired with conventional, pharmaceutically acceptable excipients and additives. Normally, the lyophilised extract is incorporated in such a composition in a concentration that depends on of the type of surface wound to be healed and the circumstances, under which the composition is to be used. For instance, a lyophilised platelet lysate extract of this invention can be applied at a concentration, such that the amount of active substance for wound healing, per $cm^2$, is equivalent to the amount of active substance found in the preparation.

Wounds

The wound to be treated in accordance with the invention is preferably a skin wound. The skin wound is preferably an ulcer.

Examples of types of wounds which can be treated with the pharmaceutical composition or platelet lysate of this invention include, but are not limited to, thermal, chemical, electrical and radiation-induced burn wounds of skin; burn wounds covered with meshed skin autografts, full thickness and partial thickness, mechanical wounds such as incisions, abrasions and lacerations; these types of wounds include also surgical and excision wounds in skin; various ulcerations of skin, such as decubitus, venous and arterial ulcers and ulcers caused by underlying diseases such as diabetes and vasculitis; corneal wounds; tympanic membrane lesions; and lesions due to pathological conditions such as bullous pemphigoid, epidermolysis bullosa and lupus erythomatosus.

This invention yet further relates promoting the healing of a surface wound (for example in skin, e.g., human skin) by applying the pharmaceutical composition of this invention to the surface of the wound.

Anal Fissure

An anal fissure is a break or tear in the skin of the anal canal. Such a fissure may be treated by applying a pharmaceutical composition of the invention or a platelet lysate of the invention to the fissure.

Vaginal Atrophy

Atrophic vaginitis (also known as vaginal atrophy or urogenital atrophy) is an inflammation of the vagina (and the outer urinary tract) due to the thinning and shrinking of the tissues, as well as decreased lubrication. It is typically caused by a decrease in secretion of the hormone estrogen. The atrophy may be treated by topically applying a pharmaceutical composition of the invention or a platelet lysate of the invention.

Wrinkle

Wrinkles treated in accordance with the invention are typically skin wrinkles. A wrinkle may be treated by applying a pharmaceutical composition of the invention or a platelet lysate of the invention to the wrinkle.

The following Examples illustrate the invention.

Example 1—Platelet Lysate

A sample of whole blood was collected and saved for analysis of the number of platelets, as a way to monitor the lysis process. The whole blood was centrifuged (120×g, 15 minutes, no break, room temperature) to separate the platelets from the remaining blood cells. The platelets ended up in the yellow plasma, known as platelet rich plasma (PRP), which was resting on top of a dark red pillar of the remaining blood cells.

A small sample of the PRP was saved to analyze the platelets, and it was show that the platelet concentration is higher compared to the whole blood as the platelets have now been concentrated in a smaller volume. The volume of the plasma differs between individuals but is related to gender such that the volume will be smaller in men and the platelet concentration in whole blood compared to PRP will therefore have increased more in men.

The PRP was transferred to another container, such as a 50 ml tube, and was then submerged in liquid nitrogen (−196° C.) until frozen or for 5 minutes. The tube was thereafter transferred to a 37° C. water bath, or other source of heat such as an incubator, until the PRP had thawed. This was referred to as one liquid nitrogen freeze/thaw cycle. This cycle was repeated three (3) more times for a total of four (4) freeze/thaw cycles. After these cycles the resulting product was referred to as C4 PL (platelet lysate) produced through 4 freeze/thaw cycles, and upon analysis it contained about 5% of the starting number of platelets in the PRP. The C4 PL contained gel lumps of platelet debris which can be removed by transferring the C4 PL to a new tube (the heavy gel lumps will fall to the bottom of the tube) or centrifuging it (3200×g, 20 minutes, with break) and using the supernatant. The C4 PL also contained microscopic debris which was visible under a microscope.

Example 2—Platelet Lysate Gel

Platelet lysate prepared as in Example 1 was transferred into a graduated sterile Falcon tube. If previously frozen, the platelet lysate was first thawed at room temperature. To the platelet lysate, calcium gluconate and plasma or thrombin were added in appropriate proportions. If the plasma was previously frozen, it was thawed at 37° C. prior to use. Appropriate proportions as were used herein include: e.g. 1: 5 parts of platelet lysate, 2 parts of plasma, 2 parts of calcium gluconate; and e.g. 2: 3 parts of platelet lysate, 1 part of thrombin, and 0.5 parts of calcium gluconate. The resulting suspension was exposed to careful slow shaking to complete 10-12×360° tube revolutions and then fractionated by size into sterile dispensation devices. Devices included syringes and micro-needle dispensers. In some instances fractionation by size was determined according to the size and shape of the ulcer to be treated.

Example 3—Platelet Lysate Gel Utility

For treatment of vaginal atrophy: 2-10 ml of plasma lysate gel with viscosity of ~1000 cps was applied intra-vaginally daily or every other day for 1-2 weeks. This was repeated for a week if symptoms recurred.

For treatment of a 5 mm diameter Diabetic foot ulcer: 2-3 ml of plasma lysate gel with viscosity of 70,000-100,000 cps was applied topically onto the ulcer daily every other day for 2-3 weeks.

REFERENCES

1. Fisher, G. J., J. Varani, and J. J. Voorhees, Looking older: fibroblast collapse and therapeutic implications. Archives of dermatology, 2008. 144(5): p. 666.
2. JAMA 293:217-228, 2005;
3. Diabetes Care 22:157-162, 1999.
4. J Invest Dermatol. 2007 May; 127(5):1018-29.
5. Clinical Diabetes Spring 2009 vol. 27 no. 2 52-58.
6. Adv Skin Wound Care. 2008 December; 21(12):568-75.
7. UK NIHR Health Technology Assessment: Randomised controlled trial of three dressing preparations (2009).
8. Schott, M. Cosmetics >>Skin Basics. [cited 2011 6 Sep.]; Available from: http://www.moritexcosmetics.com/ind-ex.php/skin-basics/.
9. Systems, R. D. Minireviews-Matrix Metalloproteinases (MMPs). 1999 [cited 2011 6 Sep.].
10. Bornstein, P., The biosynthesis of collagen. Annual Review of Biochemistry, 1974. 43(1): p. 567-603.
11. Siegel, R., Lysyl oxidase. International review of connective tissue research, 1979. 8: p. 73
12. DeGroot, J., et al., Accumulation of advanced glycation end products as a molecular mechanism for aging as a risk factor in osteoarthritis. Arthritis & Rheumatism, 2004. 50(4): p. 1207-1215.
13. Page-McCaw, A., A. J. Ewald, and Z. Werb, Matrix metalloproteinases and the regulation of tissue remodelling. Nature Reviews Molecular Cell Biology, 2007. 8(3): p. 221-233.
14. Lapière, C. M., Tadpole collagenase, the single parent of such a large family. Biochimie, 2005. 87(3-4): p. 243-247.
15. Fisher, G. J., et al., Molecular basis of sun-induced premature skin ageing and retinoid antagonism. Nature, 1996. 379(6563): p. 335-339.
16. Monnier, V. M., et al., Cross Linking of the Extracellular Matrix by the Maillard Reaction in Aging and Diabetes: An Update on "a Puzzle Nearing Resolution". Annals of the New York Academy of Sciences, 2005. 1043(1): p. 533-544.
17. Rittié, L., et al., Decreased contraction of glycated collagen lattices coincides with impaired matrix metalloproteinase production. Biochemical and biophysical research communications, 1999. 264(2): p. 488-492.
18. Vater, C., E. Harris Jr, and R. Siegel, Native cross-links in collagen fibrils induce resistance to human synovial collagenase. Biochemical Journal, 1979. 181(3): p. 639.
19. Fisher, G. J., et al., Pathophysiology of premature skin aging induced by ultraviolet light. New England Journal of Medicine, 1997. 337(20): p. 1419-1429.
20. Telgenhoff, D. and B. Shroot, Cellular senescence mechanisms in chronic wound healing. Cell Death Differ, 2005. 12(7): p. 695-8.
21. J Invest Dermatol. 2007 May; 127(5):1018-29.
22. U.S. Pat. No. 5,198,357: Preparation of a blood platelet lysate for use in a cell culture medium for hybridoma cells.
23. Vox Sang. 2009 August; 97(2):110-8. Epub 2009 Apr. 9.
24. Biologicals, Volume 39, Issue 2, March 2011, Pages 73-80.

The invention claimed is:

1. A pharmaceutical composition in the form of a gel comprising a human platelet lysate produced according to a method comprising (a) subjecting a population of human platelets to four freeze-thaw cycles, wherein the freeze portion of each cycle is carried out at a temperature lower than or equal to −190° C. and (b) mixing the platelet lysate with at least one pharmaceutically acceptable polymer and at least one pharmaceutically acceptable positively charged chemical species such that the resulting composition is an aqueous gel having a viscosity in the range of 1000 to 500,000 mPa·s (cps) at room temperature.

* * * * *